United States Patent [19]

Hwu et al.

[11] Patent Number: 5,527,683
[45] Date of Patent: Jun. 18, 1996

[54] PHOTO-INDUCED DNA-CLEAVING AGENTS

[75] Inventors: Jih R. Hwu; Shwu-Chen Tsay; Buh-Luen Chen, all of Taipei; Himatkumar V. Patel, Hsinchu; Wan-Lin Chen; Chun C. Lin, both of Taipei; Ching-Tai Chou, Hsinchu, all of Taiwan

[73] Assignee: National Science Council, Taipei, Taiwan

[21] Appl. No.: 407,582

[22] Filed: Mar. 20, 1995

[51] Int. Cl.$^6$ ............................... C12Q 1/68; C12Q 1/70; C12P 19/34; C07H 19/04
[52] U.S. Cl. ................... 435/6; 435/5; 435/91.1; 536/22.1; 536/23.1; 536/27.21; 536/28.54; 536/28.5
[58] Field of Search ............................ 564/301; 430/380; 435/91.1, 6; 536/22.1; 560/35; 210/750

[56] References Cited

U.S. PATENT DOCUMENTS 4,797,350  1/1989  Ohbayashi et al. ................ 430/380

OTHER PUBLICATIONS

Vaught et al. "Arylhydroxylamine—induced ribonucleic acid chain cleavage ad chromatographic analysis of arylamine ribonucleic acid adducts" Chem. Biol. Interactions 34: 109–124. 1981.

Sternson et al. Reaction of Phenylhydroxylamine with Bisulfite. A possible model for Amine–medicated carcinogenesis. J.Org. Chem 48: 57–60. 1983.

Jih Ru Hwu, et al., "N—Arylalkyl—N—phenylhydroxylamines as Novel Photo–induced DNA—cleaving Agents", J. Chem. Soc., Chem. Commun., Jun. 1994.

Primary Examiner—Dianne Rees
Attorney, Agent, or Firm—Hitt Chwang & Gaines

[57] ABSTRACT

The present invention discloses a photo-induced DNA-cleaving agent composition comprises N-aryl-N-(alkyl or arylalkyl)hydroxylamine having the following formula:

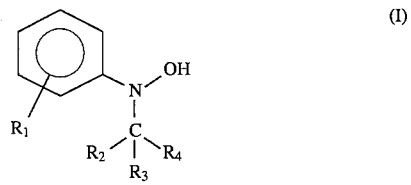

(I)

wherein R is $C_1$–$C_6$ alkyl, phenyl, $C_1$–$C_6$ alkoxy, phenoxy, $C_1$–$C_6$ alkoxycarbonyl, halogen or halo($C_1$–$C_6$ alkyl) wherein $R_1$ is hydrogen, $C_1$–$C_6$ alkyl, phenyl, $C_1$–$C_6$ alkoxy, $C_1$–$C_6$ alkoxycarbonyl, halogen or halo($C_1$–$C_6$ alkyl); $R_2$ is hydrogen; $R_3$ is hydrogen or phenyl; $R_4$ is hydrogen, phenyl, hydroxylphenyl, methoxyphenyl, dimethoxyphenyl, dimethylaminophenyl or naphthyl. The present N-aryl-N-(alkyl or arylalkyl)hydroxylamine is stable in dark, but it can react with $O_2$ to form HO. radicals under irradiation of UV light for a period of 2–3 hours. The HO. radicals then react with DNA to accomplish cleavage of DNA.

13 Claims, 1 Drawing Sheet

PHOTO-INDUCED DNA-CLEAVING AGENTS

FIELD OF THE INVENTION

The present invention relates to a photo-induced DNA-cleaving agent composition, in particular to the use of N-aryl-N-(alkyl or arylalkyl)hydroxylamine as a photo-induced DNA-cleaving agent.

BACKGROUND OF THE INVENTION

Chemists in the field of molecular design and synthesis are devoting considerable effort towards the development of DNA-cleaving agents. For recent, representative examples, there are K. M. Hess and T. A. Dix, Anal. Biochem., 1992, 206, 309; K. C. Nicolaou, W.-M. Dai, S.-C. Tsay, V. A. Estevez and W. Wrasidlo, Science, 1992, 256, 1172; M. Sako, K. Nagai and Y. Maki, J. Chem. Soc., Chem. Commun., 1993, 750. The prior art DNA-cleaving agents are in general difficult to synthesize and thus have a high manufacturing cost. In addition, the DNA-cleavage processes of using these DNA-cleaving agents often require additional metal ions, an external sensitizer or $H_2O_2$, and thus are somewhat complicated or not easy to controll, so that the cleavage efficiency is low and can be further improved.

SUMMARY OF THE INVENTION

The present invention provides a novel and efficient photo-induced DNA-cleaving agent composition which is capable of cleaving DNA under controllable conditions. The present photo-induced DNA-cleaving agent composition comprises N-aryl-N-(alkyl or arylalkyl)hydroxylamine having the formula (I):

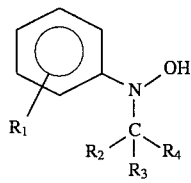

wherein $R_1$ is hydrogen, $C_1$–$C_6$ alkyl, phenyl, $C_1$–$C_6$ alkoxy, phenoxy, $C_1$–$C_6$ alkoxycarbonyl, halogen or halo($C_1$–$C_6$ alkyl), preferably $R_1$ is hydrogen or halogen, and most preferably $R_1$ is fluorine;

$R_2$ is hydrogen;

$R_3$ is hydrogen or phenyl;

$R_4$ is hydrogen, phenyl, hydroxylphenyl, methoxyphenyl, dimethoxyphenyl, dimethylaminophenyl or naphthyl.

Preferably, $R_3$ is hydrogen.

Preferably, $R_4$ is hydrogen, phenyl, hydroxylphenyl, or naphthyl, and most preferably $R_4$ is hydrogen.

The present invention also provide a method of single-strand cleavage of DNA, which comprises irradiating N-aryl-N-(alkyl or arylalkyl)hydroxylamine of the above formula (I) and DNA in an aqueous buffer solution having a pH value of 5–8 with UV light having a wavelength >300 nm and in the presence of oxygen for a period of 1–6 hours, preferably 2–3 hours. Said aqueous buffer solution preferably contains 10 vol % of ethanol. The concentration of said N-aryl-N-(alkyl or arylalkyl)hydroxylamine (I) in said aqueous buffer solution is preferably 10–1000 μM.

The N-aryl-N-(alkyl or arylalkyl)hydroxylamine (I) used in the present invention is stable in the dark, but it is able to react with $O_2$ to form HO. radicals under irradiation of UV light. The HO. radicals are known as an efficient DNA cleaver. [T. D. Tullius, B. A. Dombroski, M. E. A. Churchill and L. Kam, Methods Enzymol., 1987, 155, 537; J. A. Imlay, S. M. Chin and S. Linn, Science, 1988, 240, 640; D. S. Sigman, Biochemistry, 1990, 29, 9097]

DETAILED DESCRIPTION OF THE INVENTION

Figure 1:
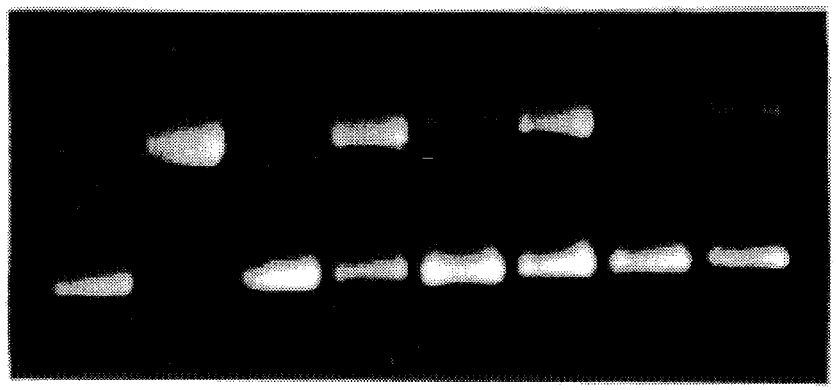
FIG. 1 shows the gel electrophoresis results of single-strand cleavage of circular ΦX174 RFI DNA (form I, 50 μM/base pair, molecular weight $3.50 \times 10^6$, 5386 base pairs in length) to relaxed circular DNA (form II) on 1% agarose gel followed by ethidium bromide staining, wherein the even numerals lanes represent the runs where 1000 μM compound 1c in the Scheme 1 is used, and the odd numerals represent the runs where no N-aryl-N-benzylhydroxylamine is used, wherein Lanes 1–2 represent the runs carried out at a pH value of 5, Lanes 3–4 represent the runs carried out at a pH value of 6, Lanes 5–6 represent the runs carried out at a pH value of 7, and Lanes 7–8 represent the runs carried out at a pH value of 8.

In the present invention, N-aryl-N-(alkyl or arylalkyl)hydroxylamine having the following formula (I) is used as a novel and efficient DNA-cleaving agent:

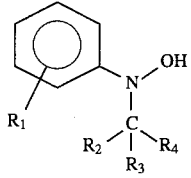

wherein $R_1$ is hydrogen, $C_1$–$C_6$ alkyl, phenyl, $C_1$–$C_6$ alkoxy, phenoxy, $C_1$–$C_6$ alkoxycarbonyl, halogen or halo($C_1$–$C_6$ alkyl);

$R_2$ is hydrogen;

$R_3$ is hydrogen or phenyl;

$R_4$ is hydrogen, phenyl, hydroxylphenyl, methoxyphenyl, dimethoxyphenyl, dimethylaminophenyl or naphthyl.

A suitable process for preparing the N-aryl-N-benzylhydroxylamine ($R_2$ and $R_3$ are hydrogen, and $R_4$ is phenyl) in high yields, as illustrated in the following Scheme 1, comprises carrying out a condensation reaction of N-arylhydroxylamines 1a–12a and benzaldehyde (PhCHO) in ethanol (EtOH) at 25° C. for 18–24 hours to form the corresponding nitrones 1b–12b; and reducing said nitrones 1b–12b with $NaBH_4$ in methanol (MeOH) at 5° C. for 10 minutes to form N-aryl-N-benzylhydroxylamines 1c–12c. In Scheme 1, Me represents methyl, Et represents ethyl and Ph represents phenyl; and the numerals in the brackets next to the compounds 1b–12b and 1c–12c represent the yields thereof.

$$\underset{X}{\overset{Y}{\bigcirc}}\!\!-\!\!\underset{H}{N}\!\!-\!\!OH \xrightarrow{(i)} \underset{X}{\overset{Y}{\bigcirc}}\!\!-\!\!\overset{+}{N}\!\!=\!\!\underset{Ph}{\overset{O^-}{CH}} \xrightarrow{(ii)} \underset{X}{\overset{Y}{\bigcirc}}\!\!-\!\!\underset{CH_2Ph}{N}\!\!-\!\!OH$$

| | | |
|---|---|---|
| 1a  X = H, Y = H        | 1b (87%)  | 1c (86%) |
| 2a  X = 4-Me, Y = H     | 2b (91%)  | 2c (84%) |
| 3a  X = 4-Et, Y = H     | 3b (81%)  | 3c (90%) |
| 4a  X = 4-Me, Y = Me    | 4b (83%)  | 4c (87%) |
| 5a  X = 2-OMe, Y = H    | 5b (85%)  | 5c (88%) |
| 6a  X = 4-OPh, Y = H    | 6b (90%)  | 6c (94%) |
| 7a  X = 2-Ph, Y = H     | 7b (90%)  | 7c (92%) |
| 8a  X = H, Y = $CO_2Me$ | 8b (94%)  | 8c (91%) |
| 9a  X = 4-F, Y = H      | 9b (97%)  | 9c (86%) |
| 10a X = H, Y = F        | 10b (97%) | 10c (72%) |
| 11a X = H, Y = $CF_3$   | 11b (85%) | 11c (75%) |
| 12a X = 2-Me, Y = F     | 12b (91%) | 12c (90%) |

Conditions: (i) PhCHO, EtOH, 25° C., 18–24 h;

(ii) $NaBH_4$, MeOH, 5° C., 10 min.

Scheme 1

A photo-induced DNA-cleaving agent composition prepared in accordance with the present invention comprises 10–1000 µM N-aryl-N-(alkyl or arylalkyl)hydroxylamine (I) in an aqueous buffer solution having a pH value of 5–8. Preferably, said aqueous buffer solution further contains 10 vol % ethanol.

The present photo-induced DNA-cleaving agent composition is suitable for single-strand cleavage of supercoiled circular form I DNA but not limited thereto.

The present invention also provides a method of single-strand cleaving DNA, which comprises irradiating N-aryl-N-(alkyl or arylalkyl)hydroxylamine of the above formula (I) and DNA in an aqueous buffer solution having a pH value of 5–8 with UV light having a wavelength >300 nm, preferably 312 nm, and in the presence of oxygen for a period of 1–6 hours, preferably 2–3 hours. Said aqueous buffer solution preferably contains 10 vol % of ethanol, for example a mixture consisting of 1:9 volume ratio of ethanol and sodium phosphate buffer solution. The concentration of said N-aryl-N-(alkyl or arylalkyl)hydroxylamine (I) in said aqueous buffer solution is preferably 10–1000 µM. The concentration of DNA in said aqueous buffer solution is preferably about 50 µM/base pair.

The present invention can be further understood by the following examples which are used to illustrate the present invention, not to limit the scope thereof.

Example 1: Effect of pH value on single-strand cleavage of DNA with or without compound 1c The compound 1c in Scheme 1 and circular ΦX174 RFI DNA (form I, molecular weight $3.50\times10^6$, 5386 base pairs in length) were added to four different mixed solutions consisting of 1:9 volume ratio of ethanol and four aqueous sodium phosphate buffer solutions having various pH values of 5, 6, 7 and 8, respectively. The concentrations of compound 1c and DNA (form I) in the mixed solutions are 1000 µM and 50 µM/base pair, respectively. The resulting solutions were irradiated with UV light (312 nm, 16-W) at room temperature under aerobic conditions for 3 hours, and then analyzed by gel electrophoresis on 1% agarose gel followed by ethidium bromide staining. The results are shown in FIG. 1. It can be seen from FIG. 1 that single-strand cleavage of circular ΦX174 RFI DNA (form I) to relaxed circular DNA (form II) occurs with compound 1c at a pH value ranging from 5 to 8 (Lanes 2, 4, 6 and 8). On the other hand, there is no relaxed circular DNA (form II) formed in the absence of compound 1c (Lanes 1, 3, 5 and 7).

Example 2: Single-strand cleavage of DNA with compounds 1c–12c at various concentrations To a mixed solution of 1:9 volume ratio of ethanol and aqueous sodium phosphate buffer solution ($Na_2HPO_4$ and $NaH_2PO_4$; 0.1M; pH=6) N-aryl-N-benzylhydroxylamine (compounds 1c–12c) and ΦX174 RFI DNA (form I, molecular weight $3.50\times10^6$, 5386 base pairs in length) were added. The concentration of DNA (form I) in the mixed solution is fixed at 50 µM/base pair. The concentrations of N-aryl-N-benzylhydroxylamines in the mixed solution are listed in Table 1. The resulting solutions were irradiated with UV light (312 nm, 16-W) at room temperature under aerobic conditions for 2 hours, and then analyzed by gel electrophoresis on 1% agarose gel followed by ethidium bromide staining. The results are shown in Table 1.

TABLE 1

| Benzyl-hydroxy-lamine | Conc. of benzylhydroxy-lamine, µM | DNA form I, % | DNA form II, % | Ratios of form II/form I |
|---|---|---|---|---|
| 1c  | 1000 | 22.3  | 77.7  | 3.5 |
| 2c  | 1000 | 36.1  | 63.9  | 1.8 |
| 3c  | 1000 | 68.3  | 31.7  | 0.46 |
| 4c  | 1000 | 67.9  | 32.1  | 0.47 |
| 5c  | 1000 | 52.3  | 47.7  | 0.91 |
| 6c  | 1000 | 80.8  | 19.2  | 0.24 |
| 7c  | 1000 | 49.1  | 50.9  | 1.0 |
| 8c  | 1000 | 80.8  | 19.2  | 0.24 |
| 9c[a] | 1000 | 83.3 | 16.7  | 0.20 |
| 9c  | 1000 | <0.1  | >99.9 | >999 |
| 9c  | 500  | <0.1  | >99.9 | >999 |
| 9c  | 100  | 31.3  | 68.7  | 2.2 |
| 9c  | 50   | 41.9  | 58.1  | 1.4 |
| 9c  | 10   | 58.4  | 41.6  | 0.71 |
| 9c  | 1    | 68.5  | 31.5  | 0.46 |
| 10c | 1000 | 1.2   | 98.8  | 82 |
| 11c | 1000 | 69.9  | 30.1  | 0.43 |
| 12c | 1000 | 84.0  | 16.0  | 0.19 |
| none | 0   | 96.3  | 3.7   | 0.04 |

[a] in the dark

Figure 2:
FIG. 2 shows the gel electrophoresis results of single-strand cleavage of circular ΦX174 RFI DNA (form I, 50 μM/base pair, molecular weight $3.50 \times 10^6$, 5386 base pairs in length) to relaxed circular DNA (form II) on 1% agarose gel followed by ethidium bromide staining, wherein Lane 1 represents the run where no N-aryl-N-benzylhydroxylamine is used, Lane 2 represents the run where 1000 μM compound 1c in the Scheme 1 is used, Lane 3 represents the run where 1000 μM compound 9c in the Scheme 1 is used without irradiation of UV light, Lanes 4–8 represents the runs where 500, 100, 50, 10 and 1 μM compound 9c in the Scheme 1 are used respectively.

The results in Table 1 show that compounds 1c–12c have DNA single-strand cleavage ability under aerobic conditions and UV light irradiation. Among compounds 1c–12c, p- and m-(fluorophenyl)-hydroxylamines 9c and 10c exhibit much higher potency than others. Under aerobic conditions with 1000 µM of compound 9c, the ratios of form II/form I DNA are 0.20 and >999, respectively, in the dark and with UV light. In the control run under photolytic conditions for 2 hours without addition of N-aryl-N-benzylhydroxylamine, the ratio is 0.04. Thus the UV light can be used as a "trigger" to initiate a N-aryl-N-benzylhydroxylamine for the DNA strand scission. FIG. 2 shows part of the gel electrophoresis results in Table 1.

Example 3: Synthesis of N-phenyl-N-(alkyl or arylalkyl) hydroxylamines and single-strand cleavage of DNA therewith N-phenyl-N-(alkyl or arylalkyl)hydroxylamines having the following formula (II) were synthesized:

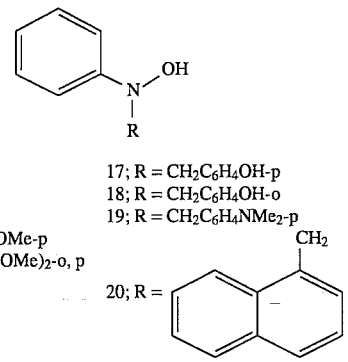

(II)

1; R = CH$_2$Ph
13; R = Me
14; R = CHPh$_2$
15; R = CH$_2$C$_6$H$_4$OMe-p
16; R = CH$_2$C$_6$H$_3$(OMe)$_2$-o, p
17; R = CH$_2$C$_6$H$_4$OH-p
18; R = CH$_2$C$_6$H$_4$OH-o
19; R = CH$_2$C$_6$H$_4$NMe$_2$-p

20; R = 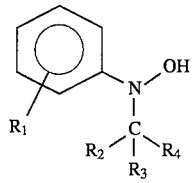

We obtained the desired hydroxylamines (1, 14–20) in 51–85% overall yields form nitrobenzene in three steps. Hydrogenation of nitrobenzene with hydrazine hydrate and rhodium on carbon gave N-phenylhydroxylamine, which was condensed with various aromatic aldehydes to afford the corresponding nitrones. Reduction of those nitrones with NaBH$_4$ in methanol (for 1, 15–20) or alkylation with PhMgBr (for 14) produced the desired N-phenyl-N-(aryl substituted)methylhydroxylamines. N-phenyl-N-methylhydroxylamine 13 was obtained by pyrolysis of MeEtPhN$^+$O$^-$ (Me represents methyl, Et represents ethyl and Ph represents phenyl).

The procedures of Example 2 were repeated to carry out single-strand cleavage of ΦX174 RFI DNA (form I, molecular weight 3.50×10$^6$, 5386 base pairs in length) to relaxed circular DNA (form II), except that the compounds 1c–12c were replaced by compounds 1, 13–20 synthesized in this example and the irradiation of UV light was 3 hours instead of 2 hours. The results are shown in Table 2.

TABLE 2

| Hydroxylamine | Conc. of hydroxylamine, μM | DNA form I, % | DNA form II, % | Ratios of form II/form I |
| --- | --- | --- | --- | --- |
| 1 | 1000 | 13.1 | 86.9 | 6.6 |
| 13 | 1000 | 31.4 | 68.6 | 2.2 |
| 14 | 1000 | 29.4 | 70.6 | 2.4 |
| 15 | 1000 | 55.1 | 44.9 | 0.81 |
| 16 | 1000 | 65.6 | 34.4 | 0.52 |
| 17 | 1000 | 48.0 | 52.0 | 1.1 |
| 18 | 1000 | 26.7 | 73.3 | 2.7 |
| 19 | 1000 | 65.4 | 34.6 | 0.53 |
| 20 | 1000 | 23.6 | 76.4 | 3.2 |
| none | 0 | 86.7 | 13.3 | 0.15 |

The present invention at least has the following advantages. First, many N-aryl-N-(alkyl or arylalkyl)hydroxylamines can be easily prepared and manipulated; thus a great potential exists for equipment of a DNA intercalating moiety or an oligonucleotide with a N-aryl-N-(alkyl or arylalkyl)hydroxylamine to give site-specific DNA cleavage. Second, use of metal ions and external H$_2$O$_2$ is not necessary. Third, the DNA cleavage process can be initiated and controlled by use of UV light as the "trigger".

What is claimed is:

1. A method of single-strand cleavage of DNA comprising the step of:

creating a mixture comprising an N-aryl-N-(alkyl or arylalkyl)hydroxylamine having formula (I) and a DNA in an aqueous buffer solution having a pH value of 5–8:

(I)

wherein

R$_1$ is hydrogen, C$_1$–C$_6$ alkyl, phenyl, C$_1$–C$_6$ alkoxy, phenoxy, C$_1$–C$_6$ alkoxycarbonyl, halogen or halo(C$_1$–C$_6$ alkyl);

R$_2$ is hydrogen;

R$_3$ is hydrogen or phenyl;

R$_4$ is hydrogen, phenyl, hydroxylphenyl, methoxyphenyl, dimethoxyphenyl, dimethylaminophenyl or naphthyl;

irradiating said mixture under an aerobic condition with a UV light having a wavelength of >300 nm for a period of 1 to 6 hours; and allowing cleavage of said DNA to occur.

2. The method of single-strand cleavage of DNA according to claim 1, wherein the concentration of said N-aryl-N-(alkyl or arylalkyl)hydroxylamine (I) in said aqueous buffer solution ranges from 10 to 1000 μM.

3. The method of single-strand cleavage of DNA according to claim 1, wherein said aqueous buffer solution contains 10 vol % of ethanol.

4. The method of single-strand cleavage of DNA according to claim 1, wherein the irradiation of the UV light ranges from 2 to 3 hours.

5. The method of single-strand cleavage of DNA according to claim 1, wherein R$_3$ is hydrogen and R$_4$ is phenyl.

6. The method of single-strand cleavage of DNA according to claim 5, wherein R$_1$ is halogen.

7. The method of single-strand cleavage of DNA according to claim 6, wherein R$_1$ is fluorine.

8. The method of single-strand cleavage of DNA according to claim 5, wherein R$_1$ is hydrogen.

9. The method of single-strand cleavage of DNA according to claim 1, wherein R$_1$ is hydrogen.

10. The method of single-strand cleavage of DNA according to claim 9, wherein R$_3$ is hydrogen and R$_4$ is naphthyl.

11. The method of single-strand cleavage of DNA according to claim 9, wherein R$_3$ is hydrogen and R$_4$ is hydroxylphenyl.

12. The method of single-strand cleavage of DNA according to claim 9, wherein R$_3$ is phenyl and R$_4$ is phenyl.

13. The method of single-strand cleavage of DNA according to claim 9, wherein R$_3$ is hydrogen and R$_4$ is hydrogen.

* * * * *

UNITED STATES PATENT AND TRADEMARK OFFICE
CERTIFICATE OF CORRECTION

PATENT NO. : 5,527,683
DATED : June 18, 1996
INVENTOR(S) : Hwu et al.

It is certified that error appears in the above-indentified patent and that said Letters Patent is hereby corrected as shown below:

In the Abstract, the 9th line following formula (I), delete "HO." and insert therefore -- HO· --.

In the Abstract, the 10th line following formula (I), delete "Ho." and insert therefore -- HO· --.

Col. 1, line 64, delete "HO." and insert therefore -- HO· --.

Col. 1, line 65, delete "HO." and insert therefore -- HO· --.

Col. 4, line 2, following "1." insert a paragraph break.

Signed and Sealed this

Fifteenth Day of October, 1996

Attest:

BRUCE LEHMAN

*Attesting Officer*  *Commissioner of Patents and Trademarks*